United States Patent
Heil et al.

(10) Patent No.: US 6,756,409 B2
(45) Date of Patent: Jun. 29, 2004

(54) PHENOXYPHENYL ALKANESULPHONATES

(75) Inventors: Markus Heil, Leichlingen (DE); Heinrich Meier, Wuppertal (DE); Paul Naab, Wuppertal (DE); Arnd Voerste, Köln (DE); Jean-Marie-Viktor De Vry, Rösrath (DE); Dirk Denzer, Solingen (DE); Frank Mauler, Overath (DE); Klemens Lustig, Wuppertal (DE); Jan-Bernd Lenfers, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/965,708

(22) Filed: Sep. 26, 2001

(65) Prior Publication Data

US 2003/0022934 A1 Jan. 30, 2003

(51) Int. Cl.⁷ ........................ A61K 31/10; C07C 309/65
(52) U.S. Cl. .................... 514/710; 514/602; 558/33; 558/48; 558/51; 564/84
(58) Field of Search ................. 514/602, 710, 514/709; 558/33, 48, 51; 564/84

(56) References Cited

FOREIGN PATENT DOCUMENTS

| WO | 9837061 | * | 8/1998 |
| WO | 0010967 | * | 3/2000 |
| WO | 0010968 | * | 3/2000 |

OTHER PUBLICATIONS

STN Internationalā CAPLUS Database, Accession No. 1991:514130; Fujisawa Pharmaceutical Co,. Ltd., Japanese Patent JP03056431 (1991), abstract.*

Consroe, *Brain Cannabinoid Systems as Targets for the Therapy of Neurological Disorders*, Neurobiol. Disease, 5:534–551, 1998.

Williamson, et al., *Cannabinoids in Clinical Practice*, Drugs 60:1303–1314, 2000.

Drysdale, et al., *Cannabinoids: Mechanisms and Therapeutic Applications in the CNS*, Curr. Med. Chem. 10:2719–2732, 2003.

* cited by examiner

*Primary Examiner*—Rita Desai
*Assistant Examiner*—Sonya Wright
(74) *Attorney, Agent, or Firm*—Susan M. Pellegrino

(57) ABSTRACT

The invention relates to novel phenoxyphenyl alkanesulphonates, processes for their preparation, their use for producing medicaments for the treatment and/or prophylaxis of diseases, in particular for the treatment of states of pain and neurodegenerative disorders.

10 Claims, No Drawings

PHENOXYPHENYL ALKANESULPHONATES

The invention relates to novel phenoxyphenyl alkanesulphonates, processes for their preparation, their use for producing medicaments for the treatment and/or prophylaxis of diseases, in particular for the treatment of states of pain and neurodegenerative disorders.

Among the constituents of the hemp plant (*Cannabis sativa*), the one of most pharmacological importance is $\Delta^9$-tetrahydrocannabinol ($\Delta^9$-THC) which causes the essential effects of cannabis on the human central nervous system (CNS). Potential historical and contemporary therapeutic applications of cannabis products comprise inter alia analgesia, emesis, anorexia, glaucoma and movement disorders.

To date, two subtypes of cannabinoid receptors and one splice variant have been identified. CB1 and CB2 receptors have seven transmembrane regions and belong to the family of G protein-coupled receptors. The CB1 receptor and the splice variant CB1a are mainly localized in the central nervous system. The CB2 receptor has been found mainly in the peripheral tissue, especially in leucocytes, spleen and macrophages.

Several classes of structures have been disclosed to date for cannabinoid receptor agonists: classical cannabinoids such as, for example, $\Delta^9$-THC, nonclassical cannabinoids such as, for example, aminoalkylindoles, and eicosanoids. The latter includes the endogenous CB1 receptor agonist anandamide.

WO-A-98/37061, WO-A-00/10967 and WO-A-00/10968 describe certain aryloxyphenyl alkanesulphonates as cannabinoid receptor agonists for the treatment of neurodegenerative disorders.

U.S. Pat. No. 3,462,473, *Biochem. Pharmacol.* 1972, 21, 1127–1134, *Fed. Proc. Fed. Amer. Soc. Exp. Biol.* 1971, 30, 841–847 and *J. Pharm. Sci.* 1973, 62, 1780–1784 disclosed certain p-phenoxyphenyl alkanesulphonates and their hypocholesterolaemic or hypolipidaemic effect.

In addition, certain phenoxyphenyl alkanesulphonates and their use as herbicides (1), antimicrobial agents (2), lubricants (3), sensitizers for heat-sensitive paper (4) and synthetic intermediates (5) are known: (1) EP-A-0 023 725; U.S. Pat. No. 3,929,903; U.S. Pat. No. 4,415,354; *Chem. Abstr.* 1979, 91, 175034 (JP-A-54066631); *Chem. Abstr.* 1981, 94, 156552 (JP-A-55154953); *Chem. Abstr.* 1981, 95, 168773 (JP-A-56046859); *Chem. Abstr.* 1981, 95, 168789 (JP-A-56079665); *Chem. Abstr.* 1989, 111, 2678 (JP-A-63104903); (2) DE-A-14 93 776; DE-A-21 31 754; U.S. Pat. No. 3,629,477; U.S. Pat. No. 3,772,445; U.S. Pat. No. 3,850,972; CH-B-450 347; CH-B-459 656; *Chem. Abstr.* 1975, 83, 72725 (JP-B-50003375); (3) U.S. Pat. No. 3,346,612; (4) U.S. Pat. No. 4,837,197; (5) *Chem. Abstr.* 1997, 127, 26629 (JP-A-09087210); *Tetrahedr.* 1990, 46, 4161–4164, *J. Am. Chem. Soc.* 1998, 39, 435–436.

It was an object of the present invention to provide cannabinoid receptor agonists with improved effect.

This object is achieved by the novel compounds according to the invention.

The present invention therefore relates to novel compounds of the general formula (I),

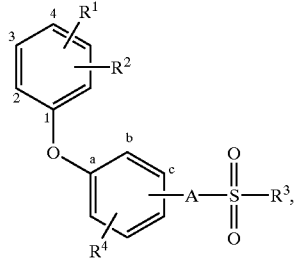

(I)

in which $R^1$ denotes hydrogen, $C_1$–$C_4$-alkyl, halogen, trifluoromethyl, trifluoromethoxy, cyano or nitro,
$R^2$ denotes halogen, trifluoromethyl, trifluoromethoxy, cyano or nitro,
$R^3$ denotes $C_4$–$C_7$-alkyl which may be substituted one or more times by fluorine or chlorine,
$R^4$ denotes hydrogen or halogen, and
A denotes oxygen or NH.

The compounds according to the invention may exist in stereoisomeric forms which either are related as image and mirror image (enantiomers) or are not related as image and mirror image (diastereomers). The invention relates to the enantiomers or diastereomers or respective mixtures thereof. These mixtures of enantiomers and diastereomers can be separated into stereoisomerically uniform components in a known manner.

The compounds according to the invention may also be in the form of their salts. Reference may generally be made here to salts with organic or inorganic bases or acids.

For the purposes of the present invention, physiologically acceptable salts are preferred. Physiologically acceptable salts of the compounds according to the invention may be salts of the substances according to the invention with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention. Particularly preferred examples are sodium, potassium, magnesium or calcium salts, and ammonium salts derived from ammonia or organic amines such as, for example, ethylamine, di- and triethylamine, di- and triethanolamine, dicyclohexylamine, dimethylaminoethanol, arginine, lysine, ethylenediamine or 2-phenylethylamine.

The present invention also includes ammonium compounds which can be prepared by converting the free amines by alkylation.

For the purposes of the present invention, the substituents generally have the following meaning:

$C_1$–$C_4$-Alkyl represents for the purposes of the invention a straight-chain or branched alkyl radical having 1 to 4 carbon atoms. Examples which may be mentioned are: methyl, ethyl, n-propyl, isopropyl, n-butyl, i-butyl, s-butyl and t-butyl.

$C_4$–$C_7$-Alkyl represents for the purposes of the invention a straight-chain or branched alkyl radical having 4 to 7 carbon atoms. Examples which may be mentioned are: n-butyl, i-butyl, s-butyl, t-butyl, i-pentyl, n-pentyl, hexyl, or heptyl. Preference is given to n-butyl, n-pentyl and n-hexyl.

Halogen includes for the purposes of the invention fluorine, chlorine, bromine and iodine. Chlorine or fluorine is preferred.

Preference is given to compounds of the general formula (I) in which $R^1$ denotes hydrogen, fluorine, chlorine, methyl, trifluoromethyl, trifluoromethoxy, cyano or nitro,
$R^2$ denotes fluorine, trifluoromethyl, trifluoromethoxy, cyano or nitro, $R^3$ denotes n-butyl, n-pentyl, 4,4,4-trifluorobut-1-yl or 5,5,5-trifluoropent-1-yl,
$R^4$ denotes hydrogen, and
A denotes oxygen.

Particular preference is given to compounds of the general formula (I)
in which $R^1$, $R^2$, $R^3$, $R^4$ and A have the abovementioned meaning, and there is a hydrogen atom in position 4 of the phenyl ring substituted by $R^1$ and $R^2$.

This can be illustrated by the following diagram:

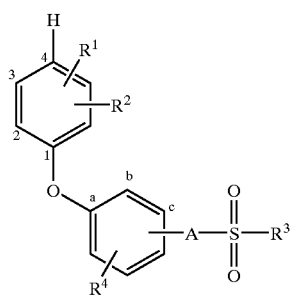

(Ia)

Very particular preference is given to compounds of the general formula (I)
in which $R^1$, $R^2$, $R^3$, $R^4$ and A have the abovementioned meaning, and
$R^1$ and $R^2$ occupy positions 2 and 3 on the phenyl ring.

The positions of $R^1$ and $R^2$ on the phenyl ring can be illustrated by the following diagram:

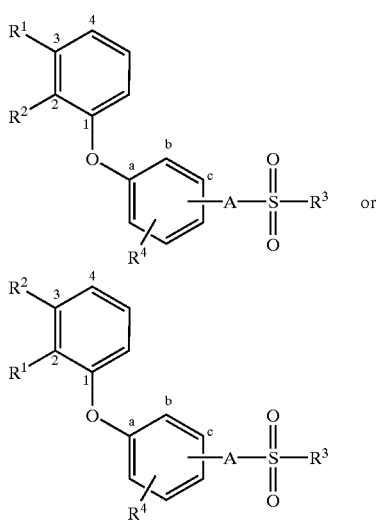

(Ib)

Very particular preference is likewise given to compounds of the general formula (I)
in which $R^1$, $R^2$, $R^3$, $R^4$ and A have the abovementioned meaning, and
A is in position c of the benzene radical.

The position of A on the benzene radical can be illustrated by the following diagram:

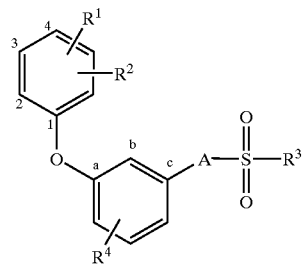

(Ic)

Very particular preference is given to compounds of the general formula (I)
in which $R^1$, $R^2$, $R^3$, $R^4$ and A have the abovementioned meaning,
$R^1$ and $R^2$ occupy positions 2 and 3 on the phenyl ring, and
A is in position c of the benzene radical.

The positions of $R^1$, $R^2$ and A can be illustrated by the following diagram:

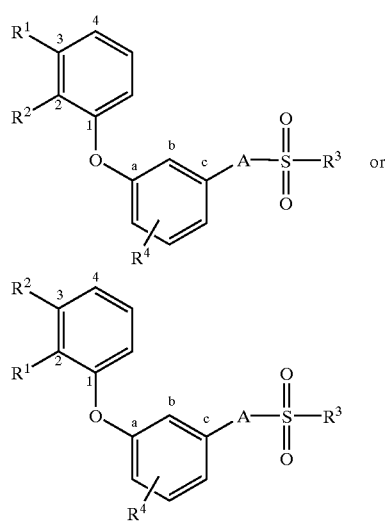

(Id)

In addition, a process for preparing compounds of the general formula (I) has been found and is characterized in that a compound of the general formula (II)

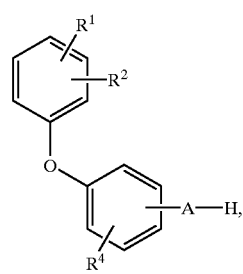

(II)

in which $R^1$, $R^2$, $R^4$ and A have the abovementioned meaning, is reacted in an inert solvent in the presence of a suitable base and, where appropriate, in the presence of a phase-transfer catalyst with a compound of the general formula (III)

$$X^1-SO_2-R^3$$ (III), in which $X^1$ represents a suitable leaving group, and
$R^3$ has the abovementioned meaning.

The compounds of the general formula (II) are novel and can be prepared in analogy to generally known processes by initially reacting a compound of the general formula (IV) with a compound of the general formula (V)

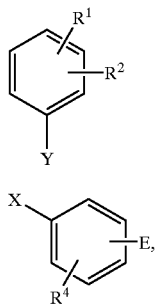
(IV)

(V)

in which $R^1$, $R^2$ and $R^4$ have the abovementioned meaning,
a) Y represents a hydroxyl group and X represents a suitable leaving group or conversely
b) Y represents a suitable leaving group and X represents a hydroxyl group, and
E represents a nitro group or a group of the formula —O—$R^5$, in which $R^5$ represents a suitable hydroxyl protective group, in an inert solvent in the presence of a suitable base and, where appropriate, in the presence of a copper(I) or copper (II) compound to give a compound of the general formula (VI)

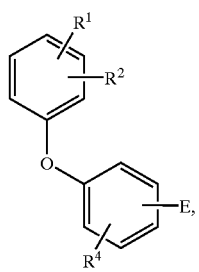
(VI)

in which $R^1$, $R^2$, $R^4$ and E have the abovementioned meaning, and

[A] then, in the case where E represents a nitro group, reducing the latter under suitable conditions by conventional methods to give a compound of the general formula (IIa)

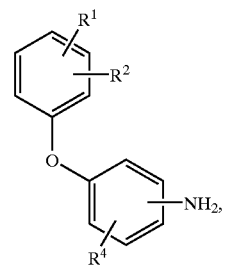
(IIa)

in which $R^1$, $R^2$ and $R^4$ have the abovementioned meaning, or

[B] in the case where E represents a group of the formula —O—$R^5$, removing the protective group $R^5$ under suitable conditions by conventional methods to liberate a compound of the general formula (IIb)

(IIb)

in which $R^1$, $R^2$ and $R^4$ have the abovementioned meaning.

The compounds of the general formula (II) can also be prepared by reacting a compound of the general formula (IV) with a compound of the general formula (VII)

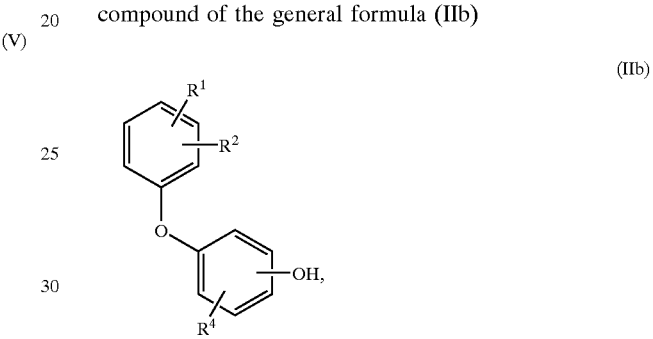
(IV)

(VII)

in which $R^1$, $R^2$, $R^4$, A, X and Y have the abovementioned meaning,
in an inert solvent in the presence of a suitable base and, where appropriate, in the presence of a copper(I) or copper(II) compound.

The processes according to the invention can be illustrated by way of example by the following diagram:

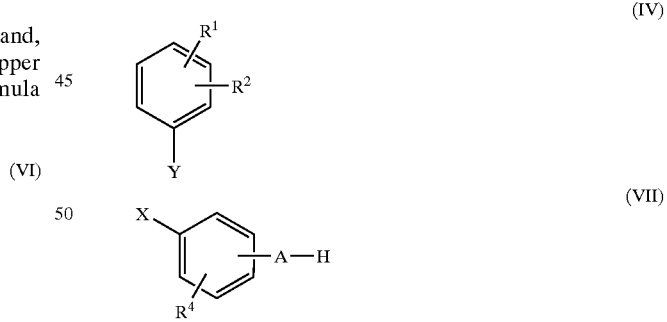

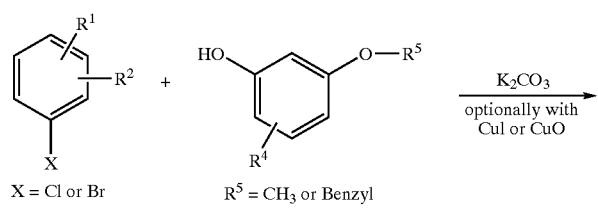

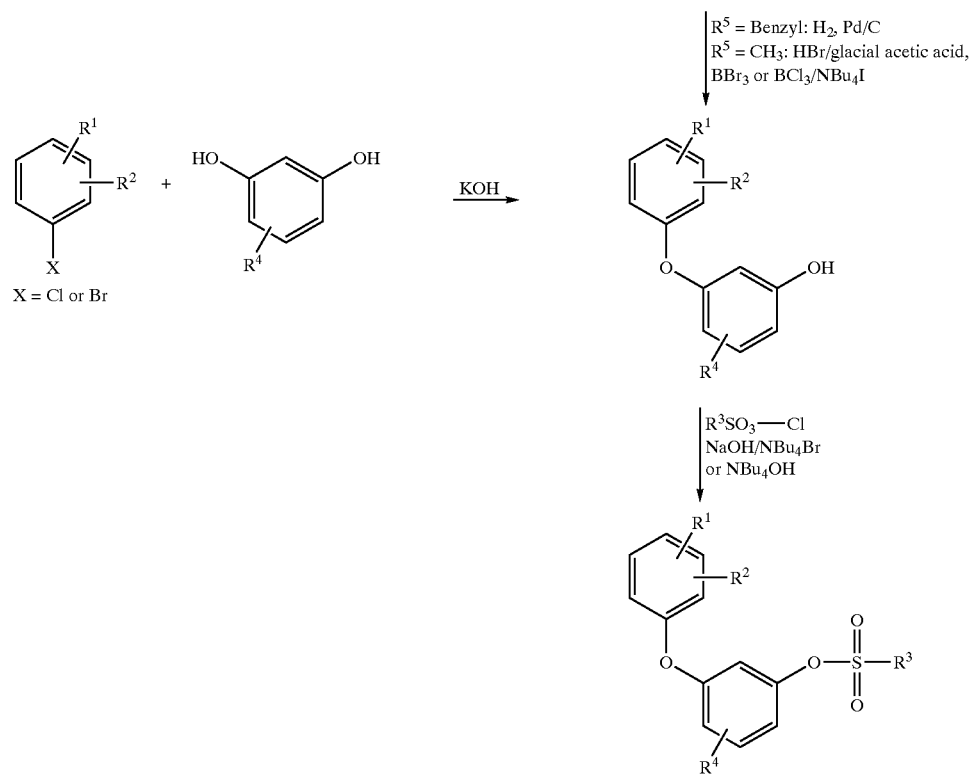

Inert solvents for the purpose of the invention are solvents which are unchanged or are only inconsiderably changed under the chosen reaction conditions.

Examples of inert solvents suitable for the process (II)+(III)→(I) are ethers such as, for example, diethyl ether, glycol monomethyl or dimethyl ether, dioxane or tetrahydrofuran, or hydrocarbons such as benzene, toluene, xylene, cyclohexane or petroleum fractions or halogenated hydrocarbons such as methylene chloride, chloroform, tetrachloromethane, or dimethyl sulphoxide, dimethylformamide, hexa-methylphosphoramide, ethyl acetate, pyridine, triethylamine or picoline. It is likewise possible to use mixtures of the said solvents, where appropriate also with water. Methylene chloride, methylene chloride/water, tetrahydrofuran, dioxane and dioxane/water are particularly preferred.

Bases suitable for reaction (II)+(III)→(I) are organic amines, in particular tri-$(C_1-C_6)$-alkylamines such as, for example, triethylamine or diisopropylethylamine, or heterocycles such as pyridine, methylpiperidine, piperidine or N-methylmorpholine, alkali metal and alkaline earth metal hydroxides or carbonates such as, for example, sodium hydroxide, potassium hydroxide, sodium carbonate, potassium carbonate or alcoholates such as, for example, sodium methanolate or sodium ethanolate. Triethylamine, pyridine and sodium hydroxide are preferred.

The bases are generally employed in an amount of from 0.1 mol to 5 mol, preferably from 1 mol to 3 mol, in each case based on 1 mol of the compounds of the general formula (II).

The process (II)+(III)→(I) can also where appropriate be carried out in the presence of a phase-transfer catalyst. Quaternary ammonium salts, preferably tetrabutylammonium bromide, for example are suitable as phase-transfer catalyst.

Suitable as leaving group $X^1$ is, for example, halogen, preferably chlorine.

The reactions can be carried out under atmospheric pressure but also under elevated or reduced pressure (for example 0.5 to 3 bar). They are generally carried out under atmospheric pressure.

The process (II)+(III)→(I) is carried out in a temperature range from 0° C. to 100° C., preferably at 0° C. to 30° C.

Examples of inert solvents which have proved suitable for the processes (IV)+(V)→(VI) and (IV)+(VII)→(II) are the following: organic solvents such as ethers, such as, for example, diethyl ether, glycol monomethyl or dimethyl ether, dioxane or tetrahydrofuran, or hydrocarbons such as benzene, toluene, xylene, cyclohexane or petroleum fractions or halogenated hydrocarbons such as methylene chloride, chloroform, tetrachloromethane, or dimethyl sulphoxide, dimethylformamide, N-methylpyrrolidone, hexamethylphosphoramide, ethyl acetate, pyridine, triethylamine or picoline. It is likewise possible to use mixtures of the said solvents, where appropriate also with water. Pyridine, N-methylpyrrolidone, dimethylformamide and dimethyl sulphoxide are particularly preferred.

The processes (IV)+(V)→(VI) and (IV)+(VII)→(II) can also where appropriate be carried out in the presence of a copper(I) or copper(II) compound. Copper(I) iodide and copper(II) oxide are preferred.

Bases suitable for the processes (IV)+(V)→(VI) and (IV)+(VII)→(II) are alkali metal carbonates and bicarbonates, in particular sodium and potassium carbonates, alkali metal hydroxides, in particular sodium hydroxide, or organic amines, in particular tri-($C_1$–$C_6$)-alkylamines such as, for example, triethylamine. Potassium hydroxide, sodium hydroxide and potassium carbonate are particularly preferred.

The bases are generally employed in an amount of from 0.1 mol to 5 mol, preferably from 1 mol to 3 mol, in each case based on 1 mol of the compounds of the general formula (IV) or (V).

A suitable leaving group X in process (IV)+(V)→(VI) variant a) or Y in process (IV)+(V)→(VI) variant b) is, for example, halogen or a sulphonato group such as, for example, triflate. Fluorine, chlorine or bromine are preferred.

The reactions can be carried out under atmospheric pressure but also under elevated or reduced pressure (for example 0.5 to 5 bar). They are generally carried out under atmospheric pressure.

The reactions are carried out in a temperature range from 20° C. to 200° C., preferably at 100° C. to 160° C.

Methods for reducing an aromatic nitro group for process step (VI)→(IIa) are known (for example R. C. Larock, "Comprehensive Organic Transformations", New York, 1989, pp. 411–415 and the literature cited therein).

The introduction of hydroxyl protective groups and methods for elimination thereof are known (for example T. W. Greene, P. G. M. Wuts, "Protective Groups in Organic Synthesis", $2^{nd}$ Ed., New York, 1991 and the literature cited therein; J. Org. Chem. 1999, 64, 9719–9721).

Examples of suitable protective group $R^5$ for the reaction sequence (IV)+(V)→(VI)→(IIb) are methyl, benzyl, allyl, methoxymethyl, 2-trimethylsilylethoxymethyl or trimethylsilyl. Methyl and benzyl are preferred.

The compounds of the general formula (III) are commercially available, known from the literature or can be synthesized in analogy to processes known from the literature (compare, for example, J. Chem. Soc. C 1968, 1265; Chem. Ber. 1967, 100, 1696; fluorinated alkanesulphonyl chlorides can be obtained, for example, as described in WO-A-98/37061 or DE-A-19 422 64).

The compounds of the general formulae (IV), (V) and (VII) are known or can be prepared by known processes.

The compounds of the general formulae (IV) and (V) are commercially available, known from the literature or can be prepared in analogy to processes known from the literature (compare, for example, J. March, "Advanced Organic Chemistry", $4^{th}$ Ed., Wiley, 1992, pages 531–534 and 1295 and the literature cited therein; Synthesis 1990, 1145–1147).

Surprisingly, the compounds according to the invention show a valuable range of pharmacological actions which could not have been predicted.

They are distinguished by being highly effective cannabinoid receptor agonists with high metabolic stability and high oral bioavailability. They are thus particularly suitable for oral therapy.

They can be employed alone or in combination with other medicaments for the prophylaxis and treatment of acute and/or chronic pain (for a classification, see "Classification of Chronic Pain, Descriptions of Chronic Pain Syndromes and Definitions of Pain Terms", $2^{nd}$ edition, Meskey and Begduk, editors; IASP-Press, Seattle, 1994) and neurodegenerative disorders, in particular for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. These substances are in addition also suitable for the therapy of primary acute pain of any origin and of secondary states of pain resulting therefrom, and for the therapy of states of pain which were formerly acute and have become chronic.

Suitable for combination with the compounds according to the invention for the treatment of acute and/or chronic pain are, for example, opiates, for example tramadol, morphine, dihydrocodeine, dextropropoxyphen, tricyclic antidepressants, for example amitriptyline, anticonvulsants, for example carbamazepine, gabapentine, non-steroidal antiinflammatory drugs (NSAIDs), for example aspirin, ibuprofen, naproxen, including COX-2 inhibitors, for example rofecoxib, celecoxib.

The compounds according to the invention are likewise also suitable for the therapy of primary and/or secondary pathological states of the brain, for example during or after cerebral vasospasms, migraine, spasticity, hypoxia and/or anoxia whose origin has not previously been mentioned, perinatal asphyxia, autoimmune diseases, metabolic and organic disorders which may be associated with damage to the brain, and damage to the brain as a consequence of primary brain disorders, for example epilepsy and atherosclerotic and/or arteriosclerotic changes. The compounds according to the invention are likewise suitable for the treatment of chronic or psychiatric disorders such as, for example, depression, gastric ulcers, neurodegenerative disorders such as, for example, Alzheimer's, Parkinson's or Huntington's disease, multiple sclerosis, amyotrophic lateral sclerosis (ALS), neurodegeneration due to acute and/or chronic viral or bacterial infections and multi-infarct dementia.

They can furthermore be employed in medicaments for the treatment of emesis, nausea, glaucoma, asthma, anorexia, convulsions, rheumatism, sedation and movement disorders.

The substances according to the invention are also suitable for the treatment of disorders which are caused by bacterial and/or viral infections which are based on direct and/or indirect changes in the immune system or on dysregulation with involvement of the immune system, such as, for example, for local or systemic autoimmune diseases (for example lupus erythematosus in all its variants), inflammatory and/or autoimmunologically related disorders of the joints (for example rheumatoid arthritis, inflammations related to trauma), inflammatory and/or autoimmunologically related disorders of the skeletal and muscular systems, inflammatory and/or autoimmunologically related pathological processes of the internal organs (for example Crohn's disease, ulcerative colitis, glomerulonephritis) and of the external organs (for example allergic reactions due to intake of airborne antigens) and of the central nervous system (for example multiple sclerosis, Alzheimer's disease, psychiatric disorders) and of the sensory organs, primary and/or secondary and/or autoimmunological disorders of the blood-forming system and of the immune system (for example rejection reactions, AIDS) itself, and for cutaneous disorders of inflammatory and/or immunological origin in humans and animals. These substances also act on the indirect symptoms of these disorders such as, for example, pain.

They are preferably used for the treatment of pain, spasticity, cerebral ischaemias and craniocerebral trauma.

The in vitro action of the compounds according to the invention on cannabinoid receptors can be shown by the following bioassays:

1. Rats CB1 Luciferase Reporter Gene Test

Stock cultures of a rat CHOCB1 reporter cell line were prepared by the method described in WO-A-98/37061, page 55 et seq.

The following test protocol was used for the substance screening: the stock cultures were cultivated in 50% of Dulbecco's modified Eagle medium/50% F-12 (DMEM/F12) with 10% FCS at 37° C. under 10% $CO_2$ and split 1:10 after 2 to 3 days in each case. Test cultures were seeded with 5000 cells per well in 96-well plates and cultured at 37° C. for 70 hours. The cultures were then cautiously washed with phosphate-buffered saline and reconstituted with serum-free Ultra-CHO medium (Bio-Whittaker). The substances dissolved in DMSO were diluted 1× in medium and pipetted into the test cultures (maximum DMSO final concentration in test mixture: 0.5%). 20 minutes later, forskolin was added and the cultures were then incubated in an incubator at 37° C. for 3 hours. The supernatants were then removed and the cells were lysed by adding 25 μl of lysis reagent (25 mM tris phosphate, pH 7.8 with 2 mM DTT, 10% glycerol, 3% Triton X100). Immediately thereafter luciferase substrate solution (2.5 mM ATP, 0.5 mM luciferin, 0.1 mM coenzyme A, 10 mM tricine, 1.35 mM $MgSO_4$, 15 mM DTT, pH 7.8) was added and briefly shaken, and the luciferase activity was measured using a Hamamatsu camera system.

To inactivate $G_i$ proteins, the test cultures were treated with 5 ng/ml (final concentration) pertussis toxin for 16 hours before the test.

The $IC_{50}$ values were calculated using the GraphPadPrism program (Hill equation, specifically: one-site competition).

Example 17 shows an $IC_{50}$ of 0.81 nM in this test.

2. hCB2 Luciferase Reporter Gene Test

CHOluc9 cells were stably transfected with the human CB2 receptor. Transfection, clone selection and test development were carried out in analogy to the work on the rat CB1 receptor. The following test protocol was used for pharmacological characterization of the cells and for substance testing:

The stock cultures were cultivated in 50% of Dulbecco's modified Eagle medium/50% F-12 (DMEM/F12) with 10% FCS at 37° C. under 10% $CO_2$ and split 1:10 after 2 to 3 days in each case. Test cultures were seeded with 5000 cells per well in 96-well plates in DMEM/F12 medium with 5% FCS and cultured at 37° C. for 70 hours. The medium was then removed from the cultures and replaced by serum-free Ultra-CHO medium (Bio-Whittaker). The substances dissolved in DMSO (200× final concentration) were pipetted into the test cultures (maximum DMSO final concentration in test mixture: 0.5%). 20 minutes later, forskolin was added and the cultures were then incubated in an incubator at 37° C. for 3.5 hours. The supernatants were then removed and the cells were lysed by adding 25 μl of lysis reagent (25 mM tris phosphate, pH 7.8 with 2 mM DTT, 10% glycerol, 3% Triton X100). Immediately thereafter 50 μl of luciferase substrate solution, doubly concentrated, (5 mM ATP, 1 mM luciferin, 0.2 mM coenzyme A, 10 mM tricine, 1.35 mM $MgSO_4$, 15 mM DTT, pH 7.8) were added and briefly shaken, and the luciferase activity was determined using a photomultiplier camera measuring system (Hamamatsu).

The $IC_{50}$ values were calculated using the GraphPad Prism™ program (Hill equation; specifically one-site competition).

3. Binding to Rat Cortex Membranes

Membrane protein is prepared from various tissues and from cells by standard methods. Buffer, labelled ligand, DMSO or test substance are pipetted together, then 100 μg of protein are added, and the mixture is thoroughly mixed and incubated in a waterbath at 30° C. for 60 min. After completion of the incubation time, the reaction is stopped by adding ice-cooled incubation buffer to each tube. Filtration is followed by washing with ¾ ml of incubation buffer. The filters are transferred into minivials, and the radioactivity is determined in a liquid scintillation counter.

The metabolic stability of the compounds according to the invention can be found in the following in vitro assay:

4. Microsomal Stability Investigations

The metabolic stability of the compounds according to the invention can be measured in rat liver microsomes (in analogy to *J. Pharmacol. Exp. Ther.* 1997, 283, 46–58).

To determine the microsomal stability and extrapolate to the maximum possible bioavailability (Fmax) owing to the first-pass effect in the liver (phase 1 reactions), the substance is incubated in low concentration with microsomal protein, with addition of cofactors, at 37° C. for 15 minutes.

The incubation and the sampling take place on a modified automatic pipettor from Canberra Packard.

As comparison with an example from WO-A-98/37061 shows, the compounds according to the invention are more metabolically stable in this test:

TABLE 1

| | $R^1$ | $R^2$ | Fmax [%] |
|---|---|---|---|
| Example 304 from WO-A-98/37061 | $CH_3$ | $CH_3$ | 2 |
| Example 15 | Cl | $CH_3$ | 4 |
| Example 17 | H | $OCF_3$ | 40 |

The bioavailability of the compounds according to the invention, and other pharmacokinetic parameters, can be determined in vivo in the following way:

5. Pharmacokinetics in the Rat a) Intravenous Infusion

The substance is infused through a Braunüle in a lateral tail vein directly into the blood stream over 15 minutes. A calibrated 20 ml syringe is used for accurate administration of the chosen dose and volume. A Braun Melsungen No. 152440/1 pump is used for the infusion.

b) Oral Administration

The substance is administered as bolus by gavage.

c) Sampling and Workup

Blood and Plasma

Blood samples are collected from catheterized animals (jugular vein) in heparinized tubes. The blood is centrifuged and the plasma is prepared in a suitable manner for analysis (LC-MS-MS). The plasma is stored at <−15° C. until analysed.

d) Pharmacokinetic Results

Microsomal data (rat liver microsomes) predict a maximum possible availability of up to 100%.

The pharmacokinetic parameters for Example 22 derived from the in vivo experiments (rat) are:

Oral data: (dose: 3 mg/kg): $AUC_{stand}$: 0.102 kg*h/l, $C_{max,stand}$: 0.0198 kg/l, $t_{max}$: 2.29 h, $t_{1/2}$ : 2.36 h, F: 33%.

i.v. data: (dose: 0.3 mg/kg): $AUC_{stand}$: 0.307 kg*h/l, $C_{max,stand}$: 0.5978 kg/l, $V_{SS}$: 4.12 l/kg, $t_{1/2}$ : 1.6 h.

The meanings herein are:

$AUC_{stand}$: the area, standardized to a dose of 1 mg/kg, under the plasma concentration/time curve;

$C_{max,stand}$: the maximum plasma concentration after a single administration, standardized to a dose of 1 mg/kg;

$t_{max}$: the time at which the maximum plasma concentration is reached after a single dose;

$t_{1/2}$: terminal half-life;

F: bioavailability; in this case the percentage, compared with i.v. administration, of the dose which is systemically available;

$V_{SS}$: apparent volume of distribution at the steady state.

The in vivo effect of the compounds according to the invention can be shown, for example, in the following animal models:

6. Hypothermia (Rat)

The in vivo agonistic effect on the CB1 receptor was examined in the rat hypothermia assay.

Five minutes after determining the basal body temperature via an oesophageal temperature probe, the test substance is administered (orally). A control group receives, likewise orally, only the solvent for the test substances (Cremophors EL 1–10%+distilled water). The body temperature is measured 120 and 240 minutes after oral administration. The size of the group for each dose is 5–7 animals (rats).

Rat Hypothermia Agonism Test

| Example | $ED_{-1° C.}$ [a)] [mg/kg] |
|---|---|
| 22 | 10 |

[a)]Effective dose for reducing the body temperature by 1° C.

The suitability of the compounds according to the invention for the treatment of states of pain can be shown in the following animal models:

7. Axotomy of Sciatic Branches in the Rat (Chronic Pain Model)

Under pentobarbital anaesthesia, the trifurcation of a sciatic nerve is exposed, and the peroneal and tibial branches are axotomized after the nerves have been ligated proximal of the axotomy site. Control animals undergo a sham operation. After the operation, the axotomized animals develop chronic mechanical hyperalgesia. This hyperalgesia is tested, comparing with sham-operated animals, with the aid of a pressure transducer (electronic von Frey anesthesiometer, IITC Inc.—Life Science Instruments, Woodland Hills, Calif., USA).

The substance is administered by various administration routes (i.v., i.p., orally, i.t., i.c.v., transdermally) at various times before the pain testing.

Example 22 reduces the hyperalgesia in the model at a minimally effective dose of 1 mg/kg orally (acute administration, 60 minutes before the test).

The suitability of the compounds according to the invention for example for the treatment of neurodegenerative disorders can be shown in the model of permanent focal cerebral ischaemia in the rat (MCA-O) or in the model of subdural haematoma in the rat (SDH) (WO-A-98/37061, page 60 et seq.).

The novel active substances can be converted in a known manner into conventional formulations such as tablets, coated tablets, pills, granules, aerosols, syrups, emulsions, suspensions and solutions by use of inert, nontoxic, pharmaceutically suitable carriers or solvents. In these the therapeutically active compound should be present in each case in a concentration of about 0.5 to 90% by weight of the complete mixture, that is to say in amounts which are sufficient to achieve the stated dose range.

The formulations are produced for example by extending the active substances with solvents and/or carriers, where appropriate with use of emulsifiers and/or dispersants, it being possible to use, for example in the case where water is used as diluent, where appropriate organic solvents as auxiliary solvents.

Administration takes place in a conventional way, preferably orally, transdermally or parenterally, in particular perlingually or intravenously. However, it can also take place by inhalation through the mouth or nose, for example with the aid of a spray, or topically through the skin.

In general, it has proved advantageous to administer amounts of about 0.001 to 10 mg/kg on oral administration, preferably about 0.005 to 1 mg/kg of body weight, to achieve effective results.

It may nevertheless be necessary where appropriate to deviate from the stated amounts, in particular depending on the body weight and the mode of administration, on the individual response to the medicament, the nature of its formulation and the time or interval over which administration takes place. Thus, in some cases it may be sufficient to make do with less than the aforementioned minimum amount, whereas in other cases the upper limit mentioned must be exceeded. In the case of administration of larger amounts, it may be advisable to distribute these in several individual doses over the day.

The determination of the retention time of starting compounds and preparation examples by HPLC took place under the following conditions:

Column: Kromasil C18 60*2; volume injected 1.00 µl; flow rate: 0.75 ml/min; eluent: A=0.01M aq $H_3PO_4$, B=$CH_3CN$; gradient [t(min): A/B)]:0:90/10; 0.5: 90/10; 4.5:10/90; 6.5:10/90; 7.5:90/10.

Abbreviations

| | |
|---|---|
| aq. | aqueous |
| CH | cyclohexane |
| TLC | thin layer chromatography |
| DCI | direct chemical ionization (in MS) |
| DCM | dichloromethane |

-continued

| EA | ethyl acetate |
| EI | electron impact ionization (in MS) |
| ESI | electrospray ionization (in MS) |
| HPLC | high pressure, high performance liquid chromatography |
| Me | methyl |
| MW | molecular weight |
| MS | mass spectroscopy |
| NMR | nuclear magnetic resonance spectroscopy |
| $R_f$ | retention index (in TLC) |
| $R_t$ | retention time (in HPLC) |

Starting Compounds

EXAMPLE I

3-Methoxy-1-(3-methyl-2-nitrophenoxy)benzene (Diphenyl Ether Synthesis—Method A)

14.7 g (96.0 mmol) of 3-methyl-2-nitrophenol, 53.9 g (288 mmol) of 3-bromoanisole and 18.3 g (96.0 mmol) of potassium carbonate are introduced into about 600 ml of pyridine and heated to about 140° C. The mixture is allowed to cool slightly, and 18.3 g (96 mmol) of copper(I) iodide are added. The mixture is stirred at about 140° C. for about 60 h. After removal of the solvent in vacuo, the residue is taken up in toluene and again evaporated. The residue is taken up in dichloromethane and filtered through kieselguhr. Washing with further dichloromethane is followed by washing successively with 5N HCl, 2N NaOH, 5N HCl, water and brine. The crude product obtained after drying over magnesium sulphate and concentration in vacuo is purified by Kugelrohr distillation.

Yield: 3.50 g (13%; HPLC purity 94%)
$R_f$: 0.28 (cyclohexane/ethyl acetate 5:1)
MS (EI): 259 (100%, [M]$^+$)
HPLC: retention time=4.94 min
$^1$H-NMR (300 MHz, CDCl$_3$): δ/ppm=2.37 (s, 3H), 3.78 (s, 3H), 6.1–6.65 (m, 2H), 6.67–6.74 (m, 1H), 6.83 (d, J=8 Hz, 1H), 6.99 (d, J=8 Hz, 1H), 7.14–7.32 (m, 2H).

EXAMPLE II

3-Methoxy-1-[2-(trifluoromethyl)phenoxy]benzene (Diphenyl Ether Synthesis—Method B)

50.0 g (222 mmol) of 2-bromobenzotrifluoride, 27.6 g (222 mmol) of 3-methoxyphenol and 30.7 g (222 mmol) of potassium carbonate are introduced into about 450 ml of pyridine and briefly heated to about 100° C. The mixture is allowed to cool slightly, and 17.7 g (222 mmol) of copper(II) oxide are added. The mixture is stirred under reflux (bath temperature about 140° C.) for about 48 h. After removal of the solvent in vacuo, the residue is taken up in dichloromethane and extracted with 2N hydrochloric acid. The organic phase is then washed with 1N sodium hydroxide solution and water. The crude product obtained after drying over magnesium sulphate and concentration in vacuo is purified by Kugelrohr distillation.

Yield: 37.2 g (62%; BPLC purity 98%)
$R_f$: 0.47 (cyclohexane/ethyl acetate 5:1)
MS (EI): 268 (100%, [M]$^+$)
HPLC: Retention time=5.14 min
$^1$H-NMR (200 MHz, CDCl$_3$): δ/ppm=3.79 (s, 3H), 6.56–6.65 (m, 2H), 6.71 (ddd, J=8 Hz, 2 Hz, 1 Hz, 1H), 6.97 (d, J=8 Hz, 1H), 7.17 (t, J=8 Hz, 1H) 7.25 (t, J=8 Hz, 1H), 7.46 (td, J=8 Hz, 1 Hz, 1H), 7.66 (d, J=8 Hz, 1H).

EXAMPLE III

1-[2-Cyano-3-(trifluoromethyl)phenoxy]-3-methoxybenzene (Diphenyl Ether Synthesis—Method C)

Under argon, 10.7 g (52.1 mmol) of 2-chloro-6-(trifluoromethyl)benzonitrile [Example 5 in DE-A-38 36 159; 2-chloro-6-(trichloromethyl)benzonitrile can be prepared from 2,6-dimethylbenzonitrile as in Example 3 in DE-A-2 214 058] are introduced into anhydrous DMF and, after addition of 7.19 g (52.1 mmol) of potassium carbonate and 6.46 g (52.1 mmol) of 3-methoxyphenol, stirred at 100° C. for 5 h. Then 500 ml of 2N NaOH and 200 ml of saturated brine are added. After extraction twice with about 300 ml of ether, the combined organic phases are dried over magnesium sulphate, evaporated in vacuo and flash chromatographed on 450 g of silica gel with toluene as mobile phase. Product fractions are evaporated to dryness and a little ether is added to the remaining oil. The crystals which form are filtered off with suction and washed with pentane.

Yield: 9.36 g (57%; HPLC purity 96%)
$R_f$: 0.39 (toluene)
Melting point: 68° C.
HPLC: Retention time=4.89 min
$^1$H-NMR (200 MHz, CDCl$_3$): δ/ppm=3.72 (s, 3H), 6.62–6.87 (m, 3H), 7.08 (d, J=8 Hz, 1H), 7.33 (t, J=8 Hz, 1H), 7.44 (d, J=8 Hz, 1H), 7.57 (t, J=8 Hz, 1H).

EXAMPLE IV

1-[2-Chloro-3-(trifluoromethyl)phenoxy]-3-nitrobenzene (Diphenyl Ether Synthesis—Method D)

Under argon, 1.00 g (5.09 mmol) of 2-chloro-3-(trifluoromethyl)phenol is introduced into 10 ml of DMF, and 0.72 g (5.09 mmol) of 3-fluoronitrobenzene and 0.70 g (5.09 mmol) of potassium carbonate are added. The mixture is heated to reflux for about 16 h. After cooling, the mixture is added to 50 ml of 2N sodium hydroxide solution and, after stirring for one hour, 20 ml of sodium chloride solution are added and stirring is continued for 30 minutes. The mixture is then extracted with dichloromethane, and the organic phase is dried over magnesium sulphate and concentrated in vacuo. Purification by chromatography on silica gel in cyclohexane/ethyl acetate 20:1 as mobile phase affords 0.69 g (42%, HPLC purity: 100%) of the target compound.

$R_f$: 0.39 (cyclohexane/ethyl acetate 2:1)
MS (EI): 317 (100%, [M]$^+$)
HPLC: Retention time=5.22 min
$^1$H-NMR (300 MHz, DMSO-d$_6$): δ/ppm=7.51 (dd, J=8 Hz, 2 Hz, 1H), 7.56–7.83 (m, 5H), 8.05 (dd, J=8 Hz, 2 Hz, 1H).

The following Examples V–XIII are prepared from the appropriate starting compounds in an analogous manner corresponding to process methods A or B for the starting compounds:

TABLE I

| Ex. No. | Target structure | MW | Method/ yield in % | HPLC purity in %/$R_t$ in min. | $R_f$ (mobile phase) | MS |
|---|---|---|---|---|---|---|
| V | | 293.2 | B/15 | 94/5.55 | 0.53 (CH/EA 20:1) | DCI/NH$_3$: 293 (100%, [M + H]$^+$) |
| VI | | 259.3 | A/59 | 96/5.05 | 0.31 (CH/EA 2:1) | EI: 259 (100%, [M]$^+$) |
| VII | | 268.2 | B/62 | 98/5.14 | 0.47 (CH/EA 5:1) | EI: 268 (100%, [M]$^+$) |
| VIII | | 269.1 | A/45 | 78/5.36 | 0.51 (CH/EA 2:1) | EI: 268 (90%, [M]$^+$) |
| IX | | 248.7 | A/70 | 96/5.54 | 0.55 (CH/EA 5:1) | EI: 248 (100%, [M]$^+$) |
| X | | 234.7 | A/61 | 73/5.09 | 0.46 (CH/EA 2:1) | DCI/NH$_3$: 235 (100%, [M + H]$^+$) |

TABLE I-continued

| Ex. No. | Target structure | MW | Method/ yield in % | HPLC purity in %/R$_t$ in min. | R$_f$ (mobile phase) | MS |
|---|---|---|---|---|---|---|
| XI | | 360.3 | B/45 | 96/5.67 | 0.53 (CH/EA 5:1) | ESI: 360 (100%, [M + H]$^+$) |
| XII | | 302.7 | A/77 | 89/5.36 | 0.55 (CH/EA 2:1) | ESI: 302 (100%, [M]$^+$) |
| XIII | | 360.3 | B/57 | 96/5.83 | 0.14 (CH/EA 2:1) | ESI: 360 (26%, [M H]$^+$) |

EXAMPLE XIV
3-(3-Methyl-2-nitrophenoxy)phenol
(Methyl Ether Cleavage—Method A)

Under argon, 500 mg (1.93 mmol) of 1-methoxy-3-(3-methyl-2-nitrophenoxy)benzene are introduced into 2 ml of anhydrous dichloromethane, and the solution is cooled to −20° C. At this temperature, 5.8 ml of a 1M solution of boron tribromide in dichloromethane are added. The mixture is allowed to reach 0° C. and is stirred for 1 h. Addition of water is followed by extraction with dichloromethane three times. The combined organic phases are washed with sodium bicarbonate solution, dried over magnesium sulphate and concentrated in vacuo. Chromatographic purification on silica gel in cyclohexane/ethyl acetate 30:1 as mobile phase affords 424 mg (89%) of the target compound.

R$_f$: 0.18 (cyclohexane/ethyl acetate 2:1)
MS (EI): 245 ([M]$^+$)
HPLC: Retention time=4.40 min
$^1$H-NMR (300 MHz, CDCl$_3$): δ/ppm=2.37 (s, 3H), 4.88 (broad s, 1H), 6.54 (t, J=2 Hz, 1H), 6.57–6.66 (m, 2H), 6.85 (d, J=8 Hz, 1H), 7.01 (d, J=8 Hz, 1H), 7.19 (t, J=8 Hz, 1H), 7.27 (t, J=8 Hz, 1H).

EXAMPLE XV
3-[2-Cyano-3-(trifluoromethyl)phenoxy]phenol
(Methyl Ether Cleavage—Method B)

Under argon, 10.0 g (34.1 mmol) of 1-(2-cyano-3-trifluoromethylphenoxy)-3-methoxybenzene are introduced into anhydrous dichloromethane, and 13.9 g (37.5 mmol) of tetra-n-butylammonium iodide are added. After cooling to −78° C., 120 ml of a 1N solution of boron trichloride in dichloromethane are slowly added dropwise, not allowing the temperature to rise above −70° C. The mixture is allowed to warm to RT within 2 h. The reaction mixture is poured onto 300 ml of ice-water, the mixture is extracted three times with dichloromethane, and the organic phase is washed 2× with saturated sodium bicarbonate solution and 1× with brine. Drying over magnesium sulphate is followed by flash chromatography on about 400 g of silica gel with dichloromethane. Pentane is added to the resulting oily product, which is left to crystallize.

Yield: 7.75 g (96%; HPLC purity 96%)
R$_f$: 0.16 (CH$_2$Cl$_2$)
Melting point: 108° C.
HPLC: Retention time=4.41 min
$^1$H-NMR (300 MHz, CDCl$_3$): δ/ppm=5.13 (s, 1H), 6.59–6.78 (m, 3H), 7.11 (d, J=8 Hz, 1H), 7.28 (t, J=8 Hz, 1H), 7.45 (d, J=8 Hz, 1H), 7.58 (t, J=8 Hz, 1H).

EXAMPLE XVI
3-[2-Chloro-3-(trifluoromethyl)phenoxy]phenol
(Methyl Ether Cleavage—Method C)

600 mg (1.98 mmol) of 3-methoxy-1-[2-chloro-3-(trifluoromethyl)phenoxy]-benzene are introduced into 6 ml of acetic acid and, after addition of 3.60 ml of 48% strength aqueous hydrobromic acid, heated to reflux for 4 h. Cooling is followed by dilution with water and extraction with ethyl acetate. The organic phases are washed three times with water and then dried over magnesium sulphate and concentrated in vacuo. Chromatography on silica gel in dichloromethane/cyclohexane 2:1 as mobile phase affords 484 mg (81%, HPLC purity 96%) of the target compound.

$R_f$: 0.39 (cyclohexane/ethyl acetate 2:1)
MS (EI): 288 ([M]$^+$)
HPLC: Retention time=4.80 min
$^1$H-NMR (300 MHz, DMSO-d$_6$): δ/ppm=6.37 (t, J=2 Hz), 6.44 (ddd, J=8 Hz, 2 Hz, 1 Hz, 1H), 6.59 (ddd, J=8 Hz, 2 Hz, 1 Hz, 1H), 7.20 (t, J=8 Hz, 1H), 7.39 (dd, J=8 Hz, 1 Hz, 1H), 7.56 (t, J=8 Hz, 1H), 7.68 (dd, J=8 Hz, 1 Hz, 1H), 9.69 (s, 1H).

EXAMPLE XVII
3-[3-(Trifluoromethyl)phenoxy]phenol
(Benzyl Ether Cleavage—Method D)

1.70 g (4.72 mmol) of 3-benzyloxy-1-[3-(trifluoromethyl)phenoxy]-benzene are suspended in 135 ml of tetrahydrofuran and 15 ml of ethanol in a hydrogenation vessel and, after addition of 170 mg of Pd 10% on carbon, hydrogenated under 1 atm of hydrogen at ambient temperature overnight. For working up, the catalyst is filtered off through kieselguhr, and the filtrate is concentrated and flash chromatographed on 130 g of silica gel in a cyclohexane/ethyl acetate gradient from 10:1 to 1:1.

Removal of the solvent affords 1.27 g (99%, HPLC purity 95%) of the target compound.

$R_f$: 0.28 (cyclohexane/ethyl acetate 5:1)
MS (EI): 270 ([M]$^+$)
HPLC: Retention time=4.78 min
$^1$H-NMR (200 MHz, CDCl$_3$): δ/ppm=4.97 (s, 1H), 6.53 (t, J=2 Hz, 1H), 6.56–6.67 (m, 2H), 6.85–7.01 (m, 3H), 7.22 (t, J=8 Hz, 1H), 7.34 (t, J=8 Hz, 1H).

The following Examples XVIII–XXV are prepared in an analogous way corresponding to process methods A, C or D:

TABLE II

| Ex. No. | Target structure | MW | Method/ yield in % | HPLC purity in %/ $R_t$ in min | $R_f$ (mobile phase) | MS |
|---|---|---|---|---|---|---|
| XVIII | | 279.1 | C/79 | 92/4.93 | 0.21 (CH/EA 10:1) | EI: 278 (100%, [M]$^+$) |
| XIX | | 245.2 | C/75 | 100/4.46 | 0.24 (CH/EA 5:1) | DCI/NH$_3$: 263 (100%, [M + NH$_4$]) |
| XX | | 254.2 | C/99 | 98/4.56 | 0.56 (CH/EA 2:1) | EI: 254 (100%, [M]$^+$) |
| XXI | | 255.1 | C/49 | 91/4.72 | 0.20 (CH/EA 5:1) | EI: 254 (43%, [M]$^+$) |

TABLE II-continued

| Ex. No. | Target structure | MW | Method/ yield in % | HPLC purity in %/ $R_t$ in min | $R_f$ (mobile phase) | MS |
|---|---|---|---|---|---|---|
| XXII | | 220.7 | C/80 | 94/4.44 | 0.21 (CH/EA 5:1) | EI: 220 (61%, [M]$^+$) |
| XXIII | | 245.2 | A/89 | 99/4.4 | 0.18 (CH/EA 2:1) | DCI/NH$_3$: 263 (100%, [M + NH$_4$]$^+$) |
| XXIV | | 234.7 | C/64 | 96/4.83 | 0.39 (CH/EA 2:1) | EI: 234 (100%, [M]$^+$) |
| XXV | | 270.2 | D/98 | 95/4.65 | 0.29 (CH/EA 2:1) | EI: 270 (100%, [M]$^+$) |

EXAMPLE XXVI

3-[2-Chloro-3-(trifluoromethyl)phenoxy]aniline

Under argon, 630 mg (1.98 mmol) of 1-[2-chloro-3-(trifluoromethyl)phenoxy]-3-nitrobenzene are introduced with 625 mg (9.09 mmol) of ammonium formate and 31.5 mg of 10% palladium/carbon catalyst into 7 ml of methanol. The mixture is heated to reflux for two hours. Cooling is followed by filtration through kieselguhr, washing with methanol, and the filtrate is concentrated. The residue is taken up again in dichloromethane and extracted three times with water, and the organic phases are dried over magnesium sulphate and reconcentrated. Chromatographic purification on silica gel in cyclohexane/ethyl acetate 6:1 as mobile phase affords 458 mg (72%, HPLC purity 90%) of the target compound.

$R_f$: 0.48 (cyclohexane/ethyl acetate 1:1)
MS (ESI): 288 (22%, [M+H]$^+$)
HPLC: Retention time=4.41 min
$^1$H-NMR (300 MHz, DMSO-d$_6$): δ/ppm=5.28 (s, 2H), 6.11–6.19 (m, 2H), 6.38 (ddd, J=(Hz, 2 Hz, 1 Hz, 1H), 7.03 (t, J=8 Hz, 1H), 7.33 (dd, J=8 Hz, 1 Hz, 1H), 7.54 (t, J=8 Hz, 1H), 7.63 (dd, J=8 Hz, 1 Hz).

EXAMPLE XXVII

1-[2-Cyano-3-(trifluoromethyl)phenoxy]-3-hydroxybenzene (Diphenyl Ether Synthesis—Method E)

Resorcinol [44.0 g (0.4 mol)] is partly dissolved in 170 ml of N-methylpyrrolidone, and potassium hydroxide [min. 85% pure; 34.5 g (0.52 mol)] and then 2-chloro-6-(trifluoromethyl)benzonitrile [20.5 g (0.1 mol)] are added. The mixture is stirred at 60–65° C. for 2.5 h. After addition of 300 ml of toluene and 400 ml of water, the aqueous phase is separated off and extracted once more with 300 ml of toluene. The combined organic phases are dried over MgSO$_4$ and, after filtration, concentrated. Digestion of the oily residue with 150 ml of water, filtration and drying affords pale brownish crystals.

Yield: 22 g (79% of theory; compare Example XV)

PREPARATION EXAMPLES

Example 1

3-[2-Cyano-3-(trifluoromethyl)phenoxy]phenyl 4,4,4-trifluoro-1-butane-sulphonate.

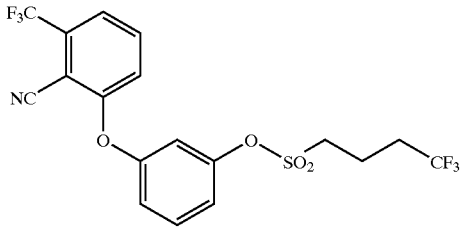

(Sulphonic Ester—Method A)

Under argon, 7.70 g (27.6 mmol) of 3-[2-cyano-3-(trifluoromethyl)phenoxy]phenol are dissolved in 60 ml of dichloromethane, and then 4.32 g (13.1 mmol) of tetrabutylammonium bromide and 3.95 ml of 45% strength NaOH are added to the solution. At 0° C., 6.64 g (31.5 mmol) of 4,4,4-trifluorobutane-1-sulphonyl chloride, dissolved in 20 ml of dichloromethane, are added in one portion. The solution becomes yellow to orange in colour and is stirred for 1 h. After subsequent dilution with water, it is extracted three times with dichloromethane. The combined organic phases are washed with brine and dried over magnesium sulphate. Purification takes place by flash chromatography on 360 g of silica gel in a stepwise gradient from 1:1 to 1:4 cyclohexane/dichloromethane as mobile phase. Rotary evaporation leaves an oily residue which is induced to crystallize by adding pentane.

Yield: 1$^{st}$ fraction 9.21 g (74%, HPLC purity 100%)
2$^{nd}$ fraction 2.29 g (18%, HPLC purity 97%)
$R_f$: 0.56 ($CH_2Cl_2$)
Melting point: 60–61° C.
MS (ESI): 454 ([M+H]$^+$)
HPLC: Retention time=5.08 min
$^1$H-NMR (300 MHz, $CDCl_3$): δ/ppm=2.2–2.5 (m, 4H), 3.39 (t, J=7 Hz, 2H), 7.0–7.3 (m, 4H), 7.50 (t, J=8 Hz, 1H), 7.53 (d, J=8 Hz, 1H), 7.64 (d, J=8 Hz).

Example 2

3-(3-Methyl-2-nitro-phenoxy)phenyl n-pentanesulphonate.

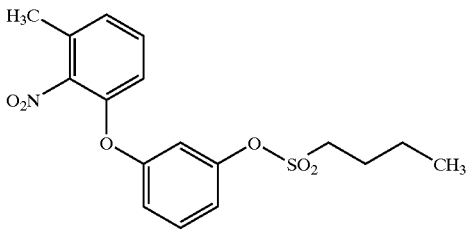

(Sulphonic Ester—Method B)

To 200 mg (0.82 mmol) of 3-(3-methyl-2-nitrophenoxy)phenol in 5 ml of dichloromethane at room temperature are added firstly 1 ml of 40% strength tetrabutylammonium hydroxide solution and then, after stirring for 5 min, 153 mg (0.90 mmol) of n-pentanesulphonyl chloride. After stirring for 1.5 h, 0.5 ml of 10% strength $NaHCO_3$ solution is added, the mixture is filtered through a 3 g extrelut cartridge (Merck Darmstadt, Order No. 115095), and the cartridge is washed several times with dichloromethane. Chromatographic purification on silica gel in cyclohexane/ethyl acetate 30:1 as mobile phase affords 255 mg (82%, HPLC purity 99%) of the target compound.

$R_f$: 0.35 (cyclohexane/ethyl acetate 2:1)
MS (ESI): 380 (100%, [M+H]$^+$)
HPLC: Retention time=5.29 min
$^1$H-NMR (300 MHz, $CDCl_3$): δ/ppm=0.93 (t, J=7 Hz, 3H), 1.30–1.51 (m, 4H), 1.89–2.02 (m, 2H), 2.39 (s, 3H), 3.18–3.28 (m, 2H), 6.85–7.42 (m, 7H).

Example 3

N-{3-[2-Chloro-3-(trifluoromethyl)phenoxy]phenyl}-4,4,4-trifluorobutane-1-sulphonamide

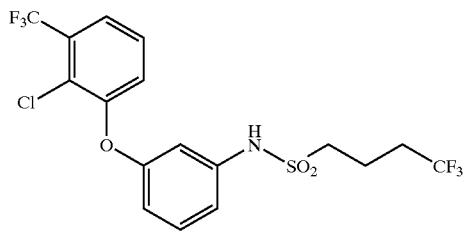

(Sulphonamide—Method C)

Under argon, 100 mg (0.35 mmol) of 3-[2-chloro-3-(trifluoromethyl)phenoxy]aniline are introduced into 1 ml of dichloromethane. 106 mg (1.04 mmol) of tnrethylamine and 77 mg (0.37 mmol) of 4,4,4-trifluorobutane-1-sulphonyl chloride, dissolved in 1 ml of dichloromethane, are added, and the mixture is stirred at room temperature. After four days, a further 0.3 equivalent of 4,4,4-trifluorobutanesulphonyl chloride is added, and stirring is continued for three days. The mixture is then extracted three times with 2N hydrochloric acid and once with saturated brine. The organic phase is dried over magnesium sulphate and concentrated in vacuo. Chromatographic purification on silica gel in dichloromethane/cyclohexane 7:2 as mobile phase affords 96 mg (54%, HPLC purity 90%) of the target compound.

$R_f$: 0.33 (cyclohexane/ethyl acetate 2:1)
MS (DCI/$NH_3$): 479 (100%, [M+$NH_4$]$^+$)
HPLC: Retention time=8.34 min
$^1$H-NMR (300 MHz, DMSO-$d_6$): δ/ppm=1.80–1.93 (m, 2H), 2.31–2.50 (m, 2H), 3.25 (t, J=8 Hz, 2H), 6.75 (dd, J=8 Hz, 2 Hz, 1H), 6.85 (t, J=2 Hz, 1H), 7.03 (dd, J=8 Hz, 1 Hz), 7.38 (t, J=8 Hz, 1H), 7.43 (dd, J=8 Hz, 1 Hz, 1H), 7.58 (t, J=8 Hz, 1H), 7.72 (dd, J=8 Hz, 1 Hz, 1H), 10.04 (s, 1H).

The following Examples 4 to 24 are prepared from the appropriate starting compounds in an analogous manner corresponding to the Preparation Example process methods A, B or C:

TABLE III
| Ex. No. | Target structure | MW | Method/ yield in % | HPLC purity in %/ $R_t$ in min | $R_f$ (mobile phase) | MS |
|---|---|---|---|---|---|---|
| 4 | 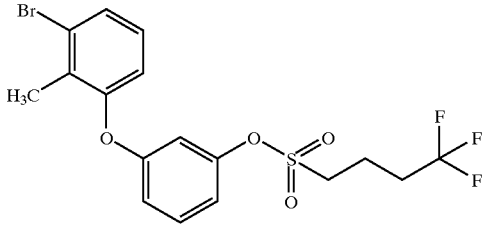 | 453.3 | A/61 | 97/5.15 | 0.33 (CH/EA 5:1) | ESI: 453 (79%, [M + H]$^+$) |
| 5 | 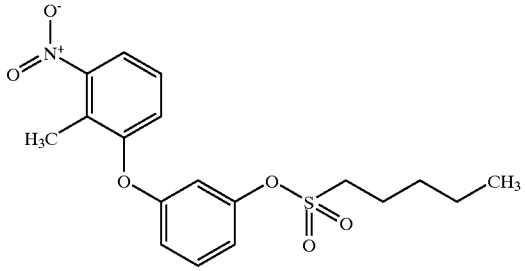 | 379.4 | A/76 | 94/5.36 | 0.63 (CH/EA 1:1) | DCI/NH$_3$: 397 (100%, [M + NH$_4$]$^+$) |
| 6 | 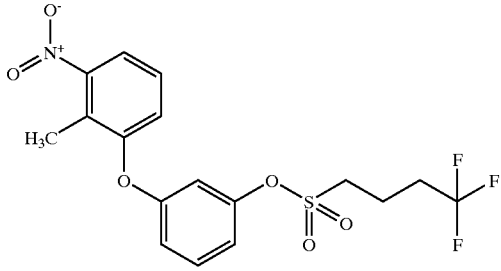 | 419.4 | B/78 | 100/5.12 | 0.69 (toluene/EA 5:1) | ESI: 420 (100%, [M + H]$^+$) |
| 7 | 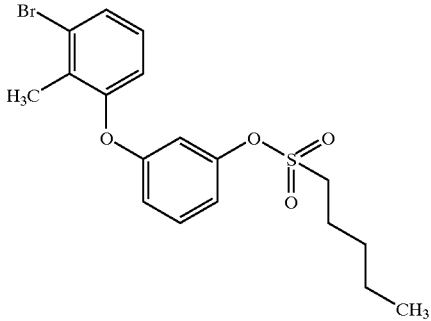 | 413.3 | A/103 | 89/5.83 | 0.52 (CH/EA 2:1) | DCI/NH$_3$: 430 (100%, [M + H]$^+$) |
| 8 | 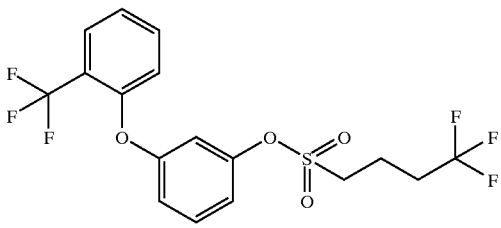 | 428.4 | A/67 | 97/5.24 | 0.32 (CH/EA 2:1) | ESI: 451 (100%, [M + Na]$^+$), ESI: 429 (89%, [M + H]$^+$) |

TABLE III-continued

| Ex. No. | Target structure | Method/ MW yield in % | HPLC purity in %/ $R_t$ in min | $R_f$ (mobile phase) | MS |
|---|---|---|---|---|---|
| 9 | | 388.4 A/79 | 94/5.47 | 0.53 (CH/EA 2:1) | ESI: 349 (35%, [M + H]$^+$) |
| 10 | | 354.9 B/63 | 81/5.44 | 0.45 (CH/EA 2:1) | DCI/NH$_3$: 372 (100%, [M + NH$_4$]$^+$) |
| 11 | | 349.8 B/67 | 81/5.2 | 0.37 (CH/EA 2:1) | DCI/NH$_3$: 412 (100%, [M + NH$_4$]$^+$) |
| 12 | | 389.3 B/76 | 100/5.64 | 0.48 (CH/EA 2:1) | DCI/NH$_3$: 406 (100%, [M + NH$_4$]$^+$) |
| 13 | | 429.2 B/72 | 97/5.38 | 0.31 (CH/EA 2:1) | DCI/NH$_3$: 446 (100%, [M + NH$_4$]$^+$) |
| 14 | | 368.9 B/84 | 93/5.77 | 0.49 (CH/EA 2:1) | DCI/NH$_3$: 386 (100%, [M + NH$_4$]$^+$) |

TABLE III-continued

| Ex. No. | Target structure | MW | Method/ yield in % | HPLC purity in %/ $R_t$ in min | $R_f$ (mobile phase) | MS |
|---|---|---|---|---|---|---|
| 15 | | 408.9 | B/69 | 92/5.5 | 0.38 (CH/EA 2:1) | DCI/NH$_3$: 426 (100%, [M + NH$_4$]$^+$) |
| 16 | | 419.4 | B/81 | 98/5.07 | 0.23 (CH/EA 2:1) | ESI: 420 (100%, [M + H]$^+$) |
| 17 | | 444.4 | A/91 | 93/5.33 | 0.25 (CH/EA 5:1) | ESI: 445 (100%, [M + H]$^+$) |
| 18 | | 404.4 | A/17 | 98/5.65 | | DCI/NH$_3$: 422 (100%, [M + NH$_4$]$^+$) |
| 19 | | 444.4 | A/29 | 96/5.4 | 0.26 (CH/EA 5:1) | ESI: 445 (57%, [M + H]$^+$) |
| 20 | | 404.4 | A/24 | 70/5.7 | | DCI/NH$_3$: 422 (100%, [M + NH$_4$]$^+$) |

TABLE III-continued

| Ex. No. | Target structure | MW | Method/ yield in % | HPLC purity in %/ R$_t$ in min | R$_f$ (mobile phase) | MS |
|---|---|---|---|---|---|---|
| 21 | | 413.4 | A/95 | 100/5.1 | 0.33 (DCM/MeOH 100:3) | ESI: 414 (100%, [M + H]$^+$) |
| 22 | | 462.8 | A/86 | 97/5.4 | 0.36 (CH/DCM 2:1) | ESI: 463 (80%, [M + H]$^+$) |
| 23 | | 422.9 | A/97 | 100/5.62 | 0.49 (CH/EA 2:1) | DCI/NH$_3$: 442 (100%, [M + NH$_4$]$^+$) |
| 24 | | 421.9 | C/48 | 91/7.94 | 0.42 (CH/EA 2:1) | DCI/NH$_3$: 439 (100%, [M + NH$_4$]$^+$) |

The abovementioned examples show the following $^1$H-NMR spectroscopic data:

TABLE IV

| Example | $^1$H-NMR (300MHz): δ/ppm |
|---|---|
| 17 | CDCl$_3$;2.17–2.42(m, 4H);3.33(t, J=7Hz, 2H);6.88(t, J=2Hz;1H) 6.92–6.95(m, 1H);7.01–7.05(ddd, H=8Hz, 2Hz, 0.5Hz;1H);7.09 (dd, J=8Hz, 2Hz, 1H);7.18–7.39(m, 4H). |
| 21 | DMSO-d$_6$;0.86(t, J=7Hz, 3H);1.24–1.43(m, 4H);1.80(quin, 2H); 3.56(t, J=7.5Hz, 2H);7.29–7.38(m, 4H);7.61(t, J=8Hz, 1H);7.77 (d, H=7.5Hz, 1H);7.88(t, J=8Hz, 1H). |
| 22 | DMSO-d$_6$;2.02(quin, 2H);2.46(m, 2H);3.69(t, J=7.5Hz, 2H); 7.02–7.08(m, 3H);7.17–7.20(dd, J=8Hz, 2Hz, 1H);7.48–7.63(m, 3H);7.72–7.75(dd, J=8Hz, 1Hz, 1H). |
| 23 | DMSO-d$_6$;0.86(t, J=7Hz, 3H);1.33(m, 4H);1.78(quin, 2H);3.52 (t, J=7.5Hz, 2H);7.02–7.06(m, 2H);7.15–7.18(m, 1H);7.48–7.64(m, 3H);7.72–7.75(dd, J=8*Hz, 1H). |

What is claimed is:
1. Compounds of the general formula (I),

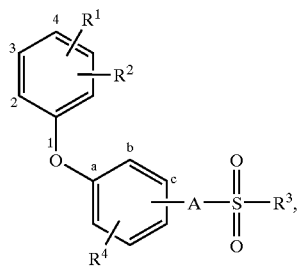

in which
R$^1$ denotes hydrogen, C$_1$–C$_4$-alkyl, halogen, trifluoromethyl, trifluoromethoxy, cyano or nitro,
R$^2$ denotes halogen, trifluoromethyl, trifluoromethoxy, cyano or nitro,
R$^3$ denotes C$_4$–C$_7$-alkyl which may be substituted one or more times by fluorine or chlorine, R⁴ denotes hydrogen or halogen, and A denotes oxygen.

2. Compounds according to claim 1,
where
- R¹ denotes hydrogen, fluorine, chlorine, methyl, trifluoromethyl, trifluoromethoxy, cyano or nitro,
- R² denotes fluorine, trifluoromethyl, trifluoromethoxy, cyano or nitro,
- R³ denotes n-butyl, n-pentyl, 4,4,4-trifluorobut-1-yl or 5,5,5-trifluoropent-1-yl,
- R⁴ denotes hydrogen, and
- A denotes oxygen.

3. Compounds according to claim 1 or 2,
where
- R¹, R², R³, R⁴ and A have the meaning stated in claim 1 or 2, and
- there is a hydrogen atom in position 4 of the phenyl ring substituted by R¹ and R².

4. Compounds according to claim 1 or 2,
where R¹, R², R³, R⁴ and A have the meaning stated in claim 1 or 2, and
R¹ and R² occupy positions 2 and 3 on the phenyl ring.

5. Compounds according to claim 1
where
- R¹, R², R³, R⁴ and A have the meaning stated in claim 1, and
- A is in position c of the benzene radical.

6. Process for preparing compounds according to claim 1, characterized in that a compound of the general formula (II)

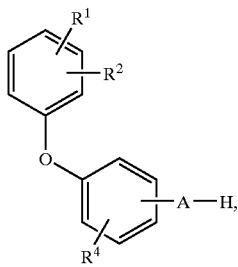

(II)

in which R¹, R², R⁴ and A have the meaning stated in claim 1, is reacted in an inert solvent in the presence of a suitable base and, where appropriate, in the presence of a phase-transfer catalyst with a compound of the general formula (III)

in which

- X¹ represents a suitable leaving group wherein the suitable leaving group is halogen, and
- R³ has the abovementioned meaning.

7. A pharmaceutical formulation containing at least one of the compounds according to claim 1 mixed with at least one pharmaceutically suitable essentially nontoxic carrier or excipient.

8. A method of treating states of pain, comprising administering to a mammal an effective amount of a compound according to claim 1, wherein said pain is acute pain, chronic pain, cancer-induced pain, chronic neuropathic pain, diabetic neuropathy, neuralgia, peripheral nerve damage, central pain, trigeminal neuralgia, lumbago, back pain, or rheumatic pain.

9. A method of treating Parkinson's disease, comprising administering to a mammal an effective amount of a compound according to claim 1.

10. A method of treating states of neurodegenerative disorders, comprising administering to a mammal an effective amount of a compound according to claim 1, wherein said neurodegenerative disorder is cerebral vasospasm, cerebral ischaemias, craniocerebral trauma, migraine, spasticity, anoxia, hypoxia, epilepsy, depression, Alzheimer's diesease, Huntington's disease, multiple sclerosis, amylotrophic lateral sclerosis.

* * * * *